United States Patent
Song et al.

(10) Patent No.: US 9,064,305 B2
(45) Date of Patent: Jun. 23, 2015

(54) METHODS AND APPARATUSES FOR GENERATING A RESPONSE OF A SCANNER IN AN IMAGING APPARATUS AND MEDICAL IMAGE USING THE SAME

(71) Applicant: Samsung Electronics Co. Ltd., Suwon-si (KR)

(72) Inventors: Tae-yong Song, Hwaseong-si (KR); Jae-mock Yi, Hwaseong-si (KR); Byung-kwan Park, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 135 days.

(21) Appl. No.: 13/965,419

(22) Filed: Aug. 13, 2013

(65) Prior Publication Data

US 2014/0093151 A1 Apr. 3, 2014

(30) Foreign Application Priority Data

Oct. 2, 2012 (KR) .................. 10-2012-0109726

(51) Int. Cl.
*G06T 7/00* (2006.01)
*G06T 11/00* (2006.01)

(52) U.S. Cl.
CPC .............. *G06T 7/0012* (2013.01); *G06T 11/005* (2013.01)

(58) Field of Classification Search
USPC ......... 382/100, 106, 128–133, 154, 254, 255, 382/286; 345/418, 422; 396/79–82; 128/922; 378/4–27
See application file for complete search history.

(56) References Cited

U.S. PATENT DOCUMENTS

| | | | | |
|---|---|---|---|---|
| 5,270,925 A | * | 12/1993 | Stegehuis | 378/7 |
| 5,878,108 A | * | 3/1999 | Baba et al. | 378/98.4 |
| 5,960,058 A | * | 9/1999 | Baba et al. | 378/98.4 |
| 6,410,920 B1 | | 6/2002 | Shao et al. | |
| 7,115,874 B2 | | 10/2006 | Peter et al. | |
| 7,660,381 B2 | * | 2/2010 | Joosten et al. | 378/7 |
| 7,920,729 B2 | * | 4/2011 | Avinash et al. | 382/128 |
| 7,983,465 B2 | | 7/2011 | Leroux et al. | |
| 8,008,625 B2 | | 8/2011 | Subbarao | |
| 8,117,142 B2 | | 2/2012 | Hu | |

(Continued)

FOREIGN PATENT DOCUMENTS

| | | |
|---|---|---|
| KR | 10-2005-0037338 A | 4/2005 |
| KR | 10-2007-0099511 A | 10/2007 |
| KR | 10-2009-0068416 A | 6/2009 |

OTHER PUBLICATIONS

Ortuño, Juan E., et al. "3D-OSEM iterative image reconstruction for high-resolution PET using precalculated system matrix." Nuclear Instruments and Methods in Physics Section A: Accelerators, Spectrometers, Detectors and Associated Equipment 569.2 (2005): 440-444.

(Continued)

*Primary Examiner* — Anand Bhatnagar
(74) *Attorney, Agent, or Firm* — NSIP Law (57) ABSTRACT

A method of generating a response from a scanner in an imaging apparatus, a method of generating a medical image, an apparatus configured to generate a response of a scanner, and an apparatus configured to generate a medical image are provided. The method of generating a response of a scanner includes: generating point spread functions (PSFs) for the amount of the acquired signal from a point source; and generating the response of the scanner for the amount of the signal acquired, based on the PSF.

21 Claims, 6 Drawing Sheets

(56) References Cited

U.S. PATENT DOCUMENTS

| | | | |
|---|---|---|---|
| 8,198,893 B2 | 6/2012 | Fath et al. | |
| 8,923,644 B2 * | 12/2014 | Kim et al. | 382/255 |
| 2007/0086560 A1 * | 4/2007 | Kia et al. | 378/7 |
| 2008/0317194 A1 | 12/2008 | Gagnon et al. | |
| 2010/0067758 A1 * | 3/2010 | Casey et al. | 382/128 |
| 2011/0007981 A1 * | 1/2011 | Osher et al. | 382/255 |

OTHER PUBLICATIONS

Panin, Vladimir Y., et al. "Fully 3-D PET reconstruction with system matrix derived from point source measurements." *Medical Imaging, IEEE Transactions on* 25.7 (2006): 907-921.

* cited by examiner

METHODS AND APPARATUSES FOR GENERATING A RESPONSE OF A SCANNER IN AN IMAGING APPARATUS AND MEDICAL IMAGE USING THE SAME

CROSS-REFERENCE TO RELATED APPLICATIONS

This application claims the benefit of Korean Patent Application No. 10-2012-0109726 filed on Oct. 2, 2012 in the Korean Intellectual Property Office, the disclosure of which is incorporated herein by reference in its entirety.

BACKGROUND

1. Field

The following description relates to methods and apparatuses for generating a response of a scanner in an imaging apparatus and the following description also relates to methods and apparatuses for generating a medical image using the system response.

2. Description of Related Art

Medical imaging devices for acquiring information about the inside of the human body and as images for diagnosis provide information necessary to diagnose diseases. Medical imaging methods currently being used or developed in hospitals are mainly classified into biological imaging techniques and anatomical imaging techniques. Representative examples of anatomical imaging techniques include Magnetic Resonance Imaging (MRI) or Computed Tomography (CT) which provide high-resolution, detailed anatomical images. These imaging techniques create two-dimensional (2D) cross-sectional images of the human body and three-dimensional (3D) images using 2D images at a high resolution. These imaging techniques show the exact locations and shapes of organs of the human body. A representative example of biological imaging techniques is Positron Emission Tomography (PET) that images the metabolic activity in the human body and detects abnormalities of the metabolic activity.

A PET imaging technique includes generating a particular radioactive tracer that emits positrons as a substance that participates in the metabolic activity inside the human body, introducing the tracer into the human body by intravenous injection or inhalation, detecting two 511-keV gamma rays that are emitted in opposite directions when positrons emitted by the tracer combine with nearby electrons by using an external device so as to track the location of the tracer, and monitoring the distribution of the tracer and a change in tracer distribution over time.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Provided are methods and apparatuses for generating a response of a scanner in a medical imaging apparatus and methods and apparatuses for generating a medical image using the response.

In one general aspect a method of generating a response of a scanner in an imaging apparatus, generally includes acquiring a signal emitted by a point source within a detection space of the scanner; generating a plurality of point spread functions (PSFs) according to the amount of the signal acquired; and generating a plurality of responses of the scanner according to the amount of the signal acquired, the plurality of responses corresponding to the number of the plurality of the PSFs.

In another general aspect a method of generating a medical image, generally includes: generating responses of a scanner in an imaging apparatus, according to the amount of a signal emitted by a point source and acquired from the scanner, based on point spread functions (PSFs) created according to the amount of the acquired signal; acquiring a subject's data by detecting a signal emitted by a tracer introduced into the subject through the scanner; determining a response for the subject among the generated responses according to the amount of the subject's data acquired; and producing a medical image by applying the determined response to the subject's data.

In another general aspect an apparatus configured to generate a response of a scanner in an imaging apparatus, includes: a scanner configured to acquire a signal emitted by a point source within a detection space; a point spread function (PSF) generator configured to generate PSFs according to the amount of the signal acquired; and a system response generator configured to generate system responses of the scanner according to the amount of the acquired signal based on the PSFs.

In another general aspect an apparatus configured to generate a medical image, includes: a response generator configured to generate responses of a scanner in an imaging apparatus, according to the amount of a signal emitted by a point source and acquired from the scanner, based on point spread functions (PSFs) created according to the amount of the acquired signal; a data acquisition unit configured to acquire for acquiring a subject's data by receiving a signal emitted by a tracer introduced into the subject from the scanner; a determination unit configured to determine a response for the subject among the generated responses, according to the amount of the subject's data acquired; and an image reconstruction unit configured to produce a medical image by applying the determined response to the subject's data.

As generally described above, methods and apparatuses are capable of generating a response for the amount of a signal, which is emitted by a point source and acquired by the scanner, by producing the system response of the scanner using a PSF created according to the amount of an acquired signal.

The methods and apparatuses are also capable of removing blur contained in subject's data by using a response for the amount of a signal acquired, thereby providing improved quality of medical images.

Other features and aspects will be apparent from the following detailed description, the drawings, and the claims.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience The units and apparatuses described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The units, devices and apparatuses described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

Figure 1:
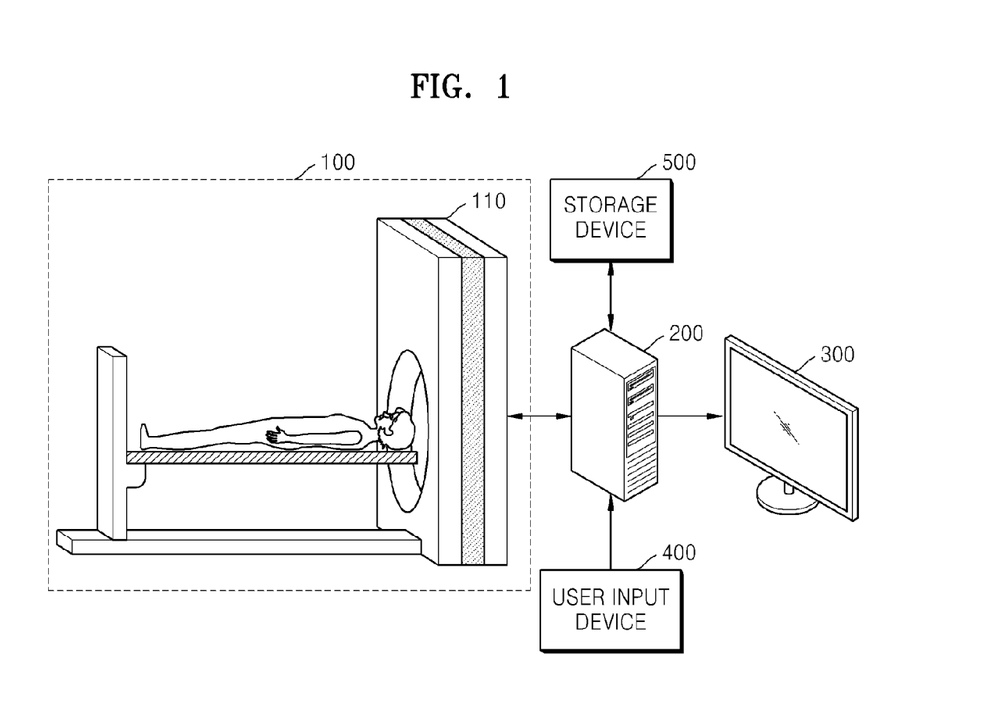
FIG. 1 illustrates a system configured to generate medical images according to an example.

FIG. 1 illustrates a system configured to generate images of cross-sections of a subject. Subject may include a human, an animal other than a human, or any other living organism. Referring to FIG. 1, the system may include an imaging apparatus 100, a computer 200, a display device 300, a user input device 400, and a storage device 500 but is not necessarily limited to that which is illustrated. The system configured to generate medical images is designed to generate not only images of cross-sections of a subject but also a response of a scanner 110 that generates the medical images. The response represents a correction model of the scanner 110.

The correction model of the scanner 110 generates high-resolution images using a signal acquired from the scanner 110, or corrects a low-resolution image into a high-resolution image. An example of the correction model may be a blur model for correcting smearing of an image.

Both a method of generating images of cross-sections of a subject in the system of FIG. 1 and a method of generating a blur model of the scanner 110 in the system of FIG. 1 will now be described in detail. A blur may refer to how far a spot or an image is scattered, or, when a position of a positron-emitting material in a detection space of the scanner 110 is estimated, how far a distribution of estimated positions is scattered or spread from an actual position of the positron-emitting material. It will be readily understood by those of ordinary skill in the art that a point spread function may be used to represent a blur.

Furthermore, the scanner acquires a signal emitted by positron-emitting materials located at respective ones of position coordinates within the detection space of the scanner 110 to create a point spread function (PSF) for each of the position coordinates. The system then combines together the PSFs to create a PSF model for the entire detection space of the scanner 110 to thereby generate a response (or blur model) for the scanner 110.

In a method of generating an image of a cross-section of a subject using the system of FIG. 1, the imaging apparatus 100 detects a signal that is emitted by a tracer injected into the subject. A positron-emitting material may be hereinafter referred to as the tracer. The imaging apparatus 100 then detects two gamma rays emitted when positrons emitted by the positron-emitting material combine with nearby electrons and transmits Line-of-Response (LOR) data associated with the detected gamma rays to the computer 200.

According to a method of generating a cross-sectional image of a patient's body using the system of FIG. 1, the imaging apparatus 100 detects a signal emitted by the tracer introduced into the patient's body. The imaging apparatus 100 then detects two gamma rays emitted by a combination of positrons emitted by the tracer and neighboring electrons and transmits LOR data associated with the detected gamma rays to the computer 200.

According to a method of generating a blur model of the scanner 110 using the system of FIG. 1, the imaging apparatus 100 detects two gamma rays emitted when positrons emitted by a point source within the scanner 110 combine with nearby electrons. The imaging apparatus 100 then transmits LOR data associated with the detected gamma rays to the computer 200. One of ordinary skill in the art will appreciate that the storage device 500, the computer 200, and display 300 may be included as part of the scanner. Other arrangements of the elements as illustrated in FIG. 1 are possible beyond that which is depicted in FIG. 1. The LOR data indicates the location of a straight line in a space, as described in more detail below with reference to FIG. 2.

Figure 2:
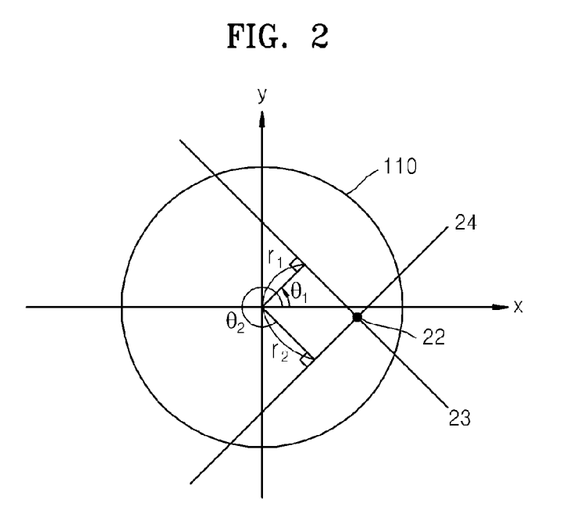
FIG. 2 is a diagram for explaining Line-of-Response (LOR) data.

FIG. 2 illustrates an example of LOR data. Referring to FIG. 2, positrons are emitted by a tracer 22 located in a subject in the scanner 110, and when the positrons react with electrons, two gamma rays are emitted at or about 180 degrees to each other and approximately form a straight line. FIG. 2 illustrates an example in which two straight lines 23 and 24 are detected. When a perpendicular line 23 is drawn from the origin within the scanner 110 on the straight line 23, a perpendicular distance between the origin and the straight line 23 is r1 and an angle between the perpendicular line and the x-axis is θ1, LOR for the straight line 23 is (r1, θ1). Similarly, when a perpendicular line 24 is drawn from the origin within the scanner 110 on the straight line 24, a perpendicular distance between the origin and the straight line 24 is r2 and an angle between the perpendicular line and the x-axis is θ2, LOR for the straight line 24 is described by (r2, θ2). When two or more amounts of LOR data are acquired, a location of a tracer may be determined from the LOR data. The imaging apparatus 100 transmits LORs for the detected gamma rays to the computer 200 which will eventually determine the location of the tracer from the LORs.

Referring to FIG. 1, the computer 200 uses data acquired from the imaging apparatus 100 to produce a medical image of the subject. In a method of generating a medical image of a subject by using the system of FIG. 1, the computer 200 uses data acquired from the imaging apparatus 100 to generate the medical image representing a cross-section of the subject. Furthermore, according to a method of generating a blur model of the scanner 110 by using the system of FIG. 1, the computer 200 uses data acquired from the imaging apparatus 100 to create the blur model of the scanner 110.

The display device 300 displays the medical image or blur model created by the computer 200 on a display panel.

The user input device 400 allows a user to input information necessary for operation of the computer 200. For example, the user input device 400 may enable a user to issue a command to start or terminate the operation of the computer 200.

When the computer 200 produces a medical image of the subject, the quality of the medical image may be affected by a spatial resolution of the scanner 110. In PET imaging, the spatial resolution may be degraded due to several factors such as, for example, an angular deviation between gamma rays, a positron range, and a geometric configuration of a scanner. The angular deviation may occur when two gamma rays are emitted by a tracer at an angle slightly greater than or less than 180 degrees, thereby resulting in degradation of a resolution of a PET image, as described in more detail below with reference to FIG. 3.

Figure 3:
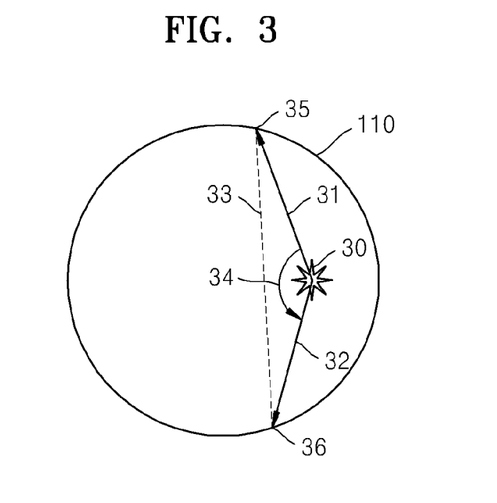
FIG. 3 illustrates an example in which two gamma rays emitted by a tracer do not form a straight line.

FIG. 3 illustrates an example in which two gamma rays 31 and 32 emitted by a tracer 30 do not form a straight line.

More specifically, FIG. 3 shows that the two gamma rays 31 and 32 are emitted from the tracer 30 at an angle slightly less than 180 degrees. The scanner 110 recognizes positions where the two gamma rays 31 and 32 are detected and assumes that the tracer 30 is on a straight line 33 joining the two positions. However, the tracer is not actually located on the straight line 33. Degradation of the resolution of a PET image due to the angular deviation significantly increases as a diameter of the scanner 110 increases.

The resolution of a PET image may also decrease due to a positron range as a positron moves away from a tracer before reaction with an electron. For example, a positron travels for a short distance after being emitted by a tracer, during which time it loses energy, and thereafter combines with and annihilates with an electron, resulting in emission of a pair of gamma rays having an energy of 511 keV. The distance that the positron travels by losing its energy is called a positron range. Since the pair of gamma rays are emitted after a positron travels for a distance corresponding to the positron range, the position of the tracer does not coincide precisely with a location where the gamma rays are emitted. Thus, when the location where the gamma rays are emitted is calculated and assumed to be the position of the tracer, an error occurs. The degradation of image resolution in PET due to this error is called a positron range effect. In general, as a positron range increases and the resolution of PET images decreases significantly with increasing positron energy.

Due to a parallax error caused by a depth of interaction (DOI) that may differ for each location due to a geometric configuration of the scanner 110, an image resolution may decrease away from a center of the scanner 110. A plurality of detectors may be closely arranged on a surface of the scanner 110. For example, when gamma rays are incident obliquely on the detectors having a rectangular shape with longer sides in a depth direction, the gamma rays may be detected coincidentally on a plurality of adjacent detectors. Thus, it is difficult to find the exact position of the tracer, and a resolution of a PET image is degraded.

The resolution of a PET image is degraded as a result of several reasons including the above-described three factors. Since some of the reasons may occur probabilistically, the resolution may be increased to a limited degree by a technical or mechanical improvement. Thus, an approach to overcoming this problem includes creating probabilistic blur information for each voxel in the scanner 110 in the form of a PSF, generating a blur model for the entire scanner 110, and applying the blur model inversely to a low-resolution PET image taken by the scanner 110 to produce a high-resolution image without blur.

Figure 4:
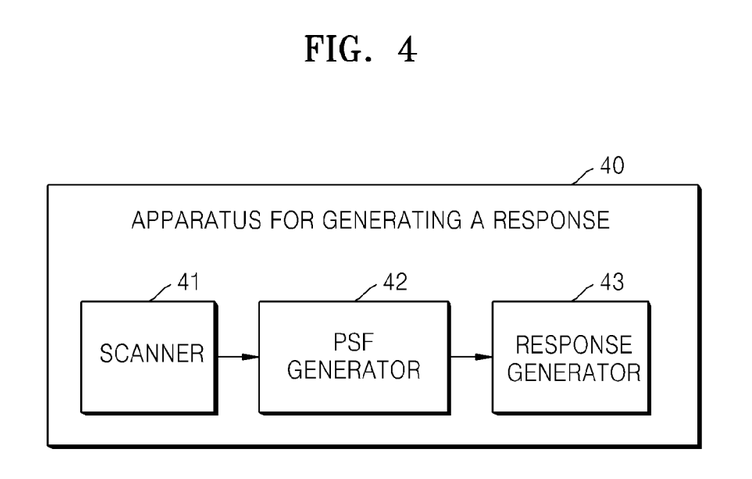
FIG. 4 illustrates an apparatus configured to generate a response according to an illustrative example.

FIG. 4 illustrates an apparatus 40 configured to generate a response. Referring to FIG. 4, the apparatus 40 includes a scanner 41, a PSF generator 42, and a response generator 43. The apparatus 40 generates a system response of the scanner 41, according to characteristics of the scanner 41. The response may be described using a matrix or function.

The scanner 41 acquires a signal generated in a detection space of the scanner. The detection space may be located on a cylindrical interior space, for example, as illustrated in FIG. 1 although other geometries of the scanner are possible. The signal may be emitted by a point source located in the detection space or by a subject into which a tracer is introduced.

In a PET device, the signal may be two gamma rays emitted when a positron emitted by a positron-emitting material introduced into a subject's body combines with a nearby electron. The scanner 41 outputs the acquired signal to the PSF generator 42.

A scanner of a PET device may have a plurality of detector blocks connected to one another and arranged on its surface. Connected may refer to connected in operation and not necessarily directly connected. Each detector block may include a plurality of detectors. The plurality of detector blocks may be arranged at predetermined angle intervals. Since each detector block may not have a curved interior surface, a cross-section of the scanner may have a polygonal shape instead of a completely circular shape.

The PSF generator 42 generates a PSF according to the amount of a signal acquired from the scanner 41. For example, the scanner 41 acquires a signal emitted by a point source that is located at a voxel in the detection space of the scanner. As the length of time taken for the scanner 41 to acquire a signal increases, the amount of the acquired signal increases. The PSF generator 42 receives the signal detected by the scanner 41 and generates PSFs for the voxel according to an increase in the amount of the acquired signal.

The PSF generator 42 presets reference values for the amount of a signal acquired and generates PSFs for each of the reference values whenever the amount of the acquired signal reaches the reference value.

For example, when the preset reference values range from first to N-th reference values, the PSF generator 42 generates N PSFs. When the amount of the acquired signal received from the scanner 41 corresponds to a first reference value, the PSF generator 42 generates a first PSF based on the received signal, the amount of which corresponds to the first reference value. When the amount of the received signal corresponds to a second reference value greater than the first reference value, the PSF generator 42 generates a second PSF based on the received signal, the amount of which corresponds to the second reference value. Thus, the PSF generator 42 generates N PSFs until the amount of the acquired signal reaches the N-th reference value. The reference values are preset based on the amount of a signal acquired from the scanner 41, wherein the signal is emitted by a point source or subject.

The response generator 43 generates responses of the scanner 41 according to the amount of the acquired signal based on the generated PSFs. The PSF is created for all voxels in the detection space of the scanner 41. The PSFs are also created for each voxel according to the amount of an acquired signal. Thus, the response generator 43 generates responses of the scanner 41 by PSFs created for each voxel according to the amount of the acquired signal.

The response generator 43 may generate system responses in a matrix form. In this case, the response generator 43 generates system matrices for preset reference values. For example, the response generator 43 generates a matrix for a first reference value by using a PSF created when the amount of an acquired signal corresponds to the first reference value. In the same manner as in generating the matrix for the first reference value, the response generator 43 generates matrices for second through N-th reference values. The response generator 43 then generates a single response by using the first through N-th matrices.

The response generator 43 also generates functions that represent the degree of blur according to the amount of an acquired signal. For example, the degree of blur may represent a kernel size that varies with the amount of the acquired signal. Aside from generating system matrices for each of the reference values having a discontinuous size, the response generator 43 may generate a continuous function which continuously represents kernel size according to the amount of the acquired signal. The response generator 43 may generate a different function for each voxel in the detection space of the scanner 41 according to an acquired signal, each function describing the degree of blur per voxel according to the amount of an acquired signal.

The PSF generator 42 or the response generator 43 may correspond to one or more processors. The one or more processors may be realized by an array of a plurality of logic gates or a combination of a general-purpose microprocessor and a memory having stored thereon a program that can be executed by the microprocessor. It will be also understood by those of ordinary skill in the art that the processors may be realized by other types of hardware.

Although the apparatus 40 of FIG. 4 includes components related to the present example, it should be readily appreciated by those of ordinary skill in the art that the apparatus 40 may further include other components not illustrated.

Figure 5:
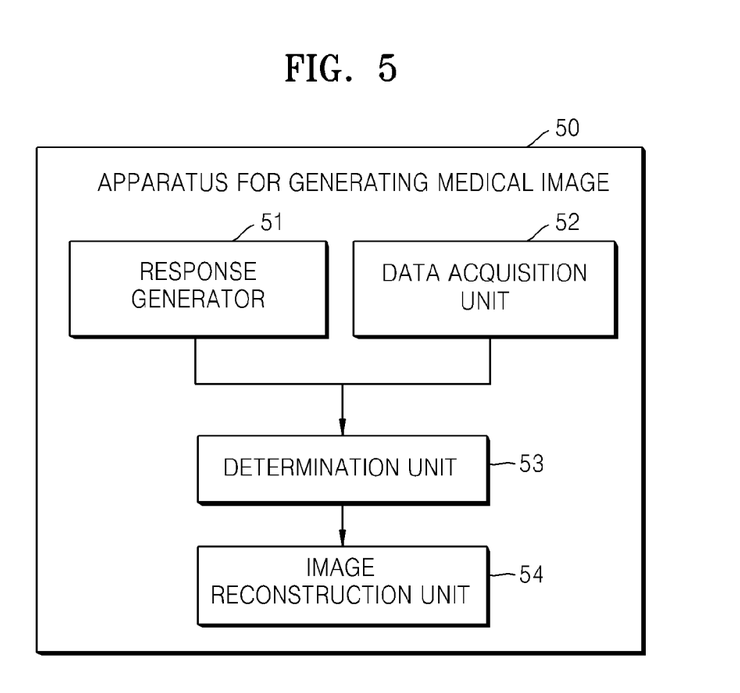
FIG. 5 illustrates an apparatus configured to generate a medical image according to an illustrative example.

FIG. 5 illustrates an apparatus 50 configured to generate a medical image according to an example. The apparatus 50 includes a response generator 51, a data acquisition unit 52, a determination unit 53, and an image reconstruction unit 54. The apparatus 50 generates a high quality medical image by using a response that is produced according to the amount of data acquired. The response generator 51, data acquisition unit 52, the determination unit 53 and the image reconstruction unit 54 may be applied in the computer 200 of the system of FIG. 1.

The response generator 51 is an example of the apparatus 40 configured to generate a system response illustrated in FIG. 4. Thus, the descriptions with respect to the apparatus 40 apply to the descriptions of the response generator unit 51 with reference to FIG. 5 although they are not repeated.

The response generator unit 51 generates responses of a scanner in an imaging apparatus, which corresponds to the amount of a signal emitted by a point source and acquired from the scanner, based on PSFs created according to the amount of the acquired signal. The response generator 51 then outputs the system responses to the determination unit 53.

The data acquisition unit 52 receives a signal which is emitted by a tracer introduced into the subject located in the scanner and acquires data related to the subject. The data acquisition unit 52 then outputs the acquired data to the determination unit 53.

The determination unit 53 determines one of the responses according to the amount of the acquired data received from the data acquisition unit 52. For example, the determination unit 53 determines a response to be applied to the subject's data among the responses received from the response generator 51.

When the responses are then input to the determination unit 53 as matrices, the determination unit 53 uses the matrices to determine a matrix to be applied to frames of the subject's data according to the amount of acquired data. Subject's data is three-dimensional data which is formed of a plurality of two-dimensional cross-sectional data (frames). The same applies to frames of a matrix. Accordingly, the determination unit 53 determines appropriate frames for frames of subject's data from among the frames of the matrix.

For example, among frames in matrices, the determination unit 53 determines as a response a frame in a matrix generated when the amount of an acquired signal is closest to the amount of subject's acquired data. The determination unit 53 determines a frame in a matrix to be applied for each frame of the subject's data and uses the determined frames to determine the overall response. When two or more matrices have an amount of acquired signal that is closest to the amount of the acquired subject's data, the determination unit 53 may select a matrix created for a larger amount of the acquired signal. The determination unit 53 may determine a matrix according to the amount of acquired subject's data by using various other methods.

In another example, when the response input to the determination unit 53 is a function, the determination unit 53 determines a function value corresponding to the amount of the acquired data received from the data acquisition unit 52 as a response to be applied to subject's data. The determination unit 53 selects a function to be applied for each voxel of the subject's data and determines a function value corresponding to the amount of acquired subject's data from the selected function.

A process of determining a response in the determination unit 53 will be described in more detail below with reference to FIGS. 6 and 7.

The determination unit 53 determines a response of each voxel according to the amount of data acquired for the voxel. For example, the determination unit 53 independently determines a response for each voxel. The amount of a subject's data acquired varies from voxel to voxel, and the degree of blur of data varies depending on the amount of acquired data. Thus, a response should vary for each voxel in the data. Thus, the determination unit 53 determines a response for each voxel in the subject's data so that a response suitable for each voxel can be used to generate a medical image.

The image reconstruction unit 54 generates a medical image by applying the determined response to the subject's data. Since the subject's data contains blur information related to the characteristics of the scanner, deblurring is needed to remove the blur information contained in the subject's data. The image reconstruction unit 54 performs deblurring by applying a response, which is a function of the characteristics of the scanner, inversely to the acquired subject's data. For example, since the subject's data includes information about the subject and blur information, the blur information may be removed from the subject's data by applying blur information of the scanner inversely to the subject's data.

The image reconstruction unit 54 applies a response determined for each voxel in the subject's data. For example, the image reconstruction unit 54 applies a response of the scanner to each voxel, wherein the response is determined according to the amount of data acquired for each of the voxels in the subject's data. Thus, applying a response suitable for each voxel in the subject's data may minimize distortion in a medical image and improve the quality of the medical image.

Figure 6:
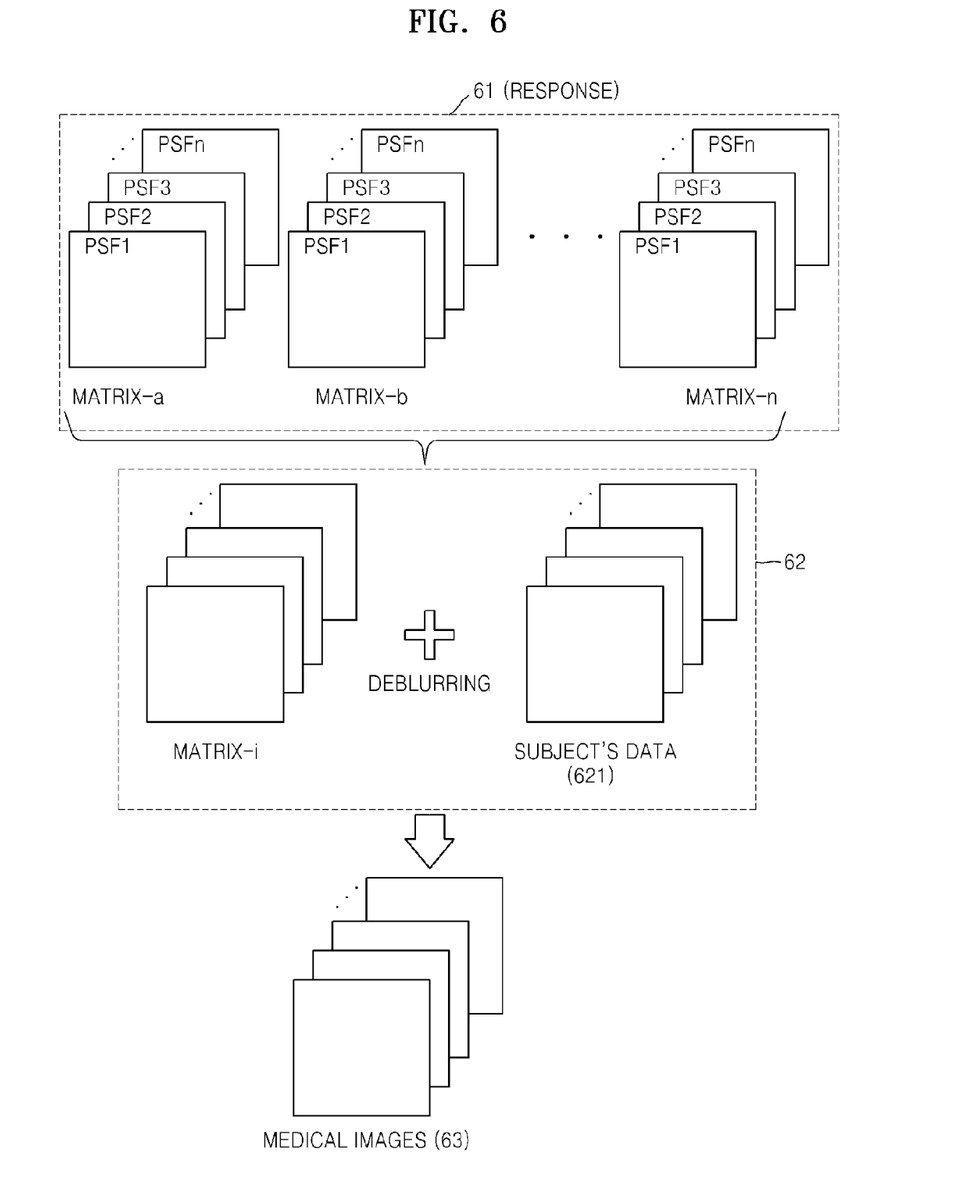
FIG. 6 is a diagram for explaining a process of generating medical images by using matrices according to an illustrative example in the apparatus of FIG. 5.

FIG. 6 is a diagram for explaining a process of generating medical images 63 by application of system matrices in the apparatus 50 of FIG. 5. Referring to FIGS. 5 and 6, the apparatus 50 configured to generate a medical image generates matrices based on the characteristics of a scanner and applies a matrix-I, which is generated by using the matrices, to a subject's data 621 acquired from a subject, and produces the medical images 63.

The response generator 51 generates matrices a through n as a response 61 of the scanner. The matrices a through n are responses of the scanner which are generated according to the amount of a signal emitted by a point source and acquired from the scanner. For example, the matrix-a is generated according to the amount of an acquired signal when the point source is located at a predetermined position of the scanner. The matrices a through n refer to responses for signals acquired at different positions in a detection space of the scanner. PSF1 through PSFn denote PSFs created according to the amount of a signal acquired.

Thereafter, the apparatus 50 applies the matrix-i to the subject's data 621 (operation 62). For example, the apparatus 50 determines the matrix-i to be applied to the subject's data 621 from the responses 61, applies the matrix-i to the subject's data 621, and produces the medical images 63 by removing blur in the subject's data 621.

For example, the apparatus 50 uses the matrices a through n to determine a matrix to be applied to deblurring of the subject's data 621. The determined matrix is denoted by matrix-i. The matrix-i denotes a matrix composed of frames determined among frames in the matrix-a through the matrix-n. The apparatus 50 determines the matrix-i according to the amount of acquired subject's data. For example, the apparatus 50 may determine a frame in a different matrix for each pixel. A frame in a matrix may represent one PSF contained in the matrices a through n.

For example, the apparatus 50 may determine a PSF 3 in the matrix-a for one voxel in the subject's data 621 and a PSF 1 in the matrix-b for another voxel. The apparatus 50 determines a frame in a matrix for each voxel according to the amount of acquired data and generates the matrix-i composed of the determined frames.

The apparatus 50 applies the matrix-i inversely to the subject's data 621 to generate the medical images 63. By way of non-limiting example, by applying frames determined for each voxel in the subject's data 621 inversely to the subject's data 621, the apparatus 50 removes a blur in the subject's data 621 to produce the medical images 63. Furthermore, the matrices may be stored in a memory in the form of a look-up table.

Figure 7:
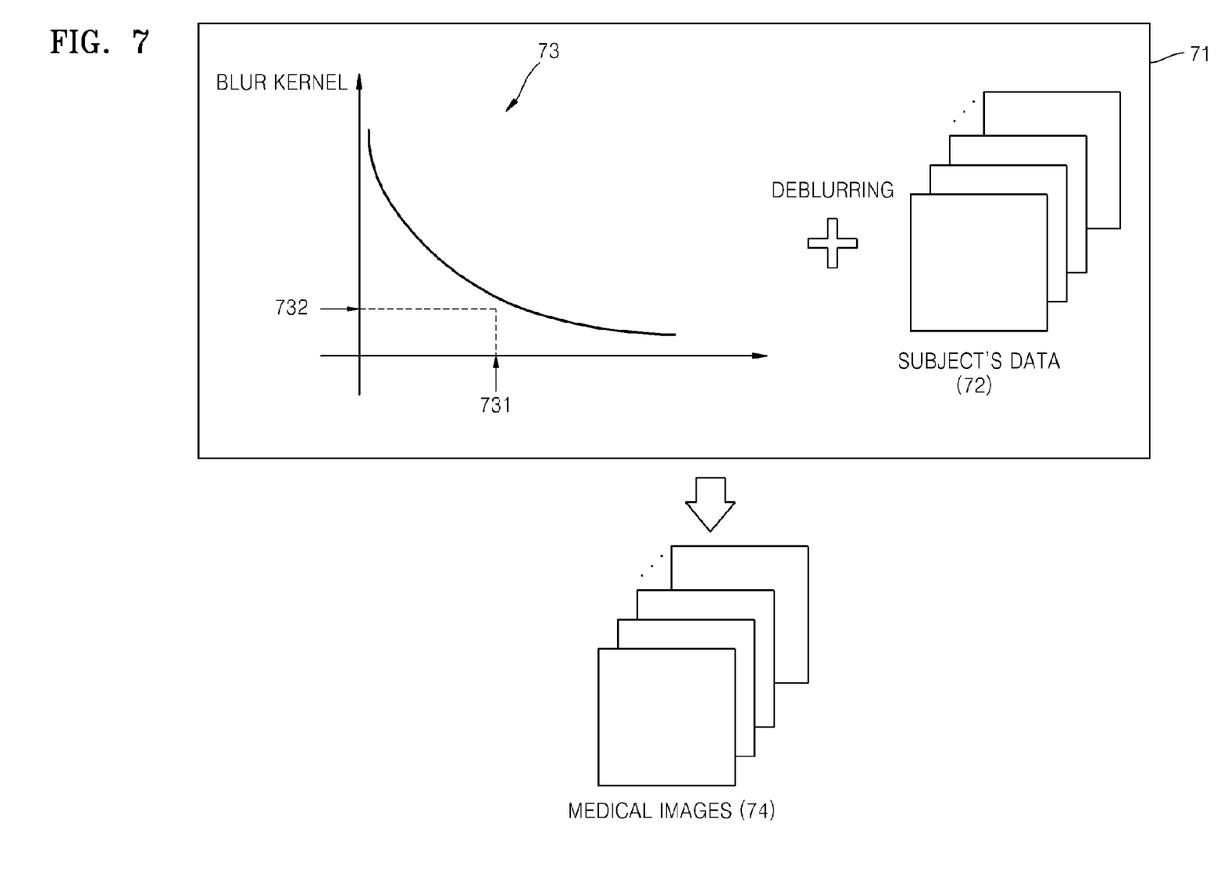
FIG. 7 is a diagram for explaining a process of generating medical images by using a function according to an illustrative example in the apparatus of FIG. 5.

FIG. 7 is a diagram for explaining a process of generating medical images 74 by using a function in the apparatus 50 of FIG. 5. Referring to FIG. 7, the apparatus 50 generates a function representing the characteristics of a scanner and applies a function value to a subject's data acquired from a subject, and produces the medical images 74.

FIG. 7 reference numeral 71 denotes an operation of determining a blur kernel to be applied to the subject's data 72. More specifically, the apparatus 50 uses a function to determine a blur kernel to be applied to the subject's data 72, applies the determined blur kernel to the subject's data, and produces the medical images 74 by removing blur in the subject's data 72.

Referring to FIG. 7, the apparatus 50 generates a function as a response of the scanner. The function represents a value of a blur kernel for the amount of a signal acquired. The blur kernel refers to the degree of blur and is used to determine the degree of deblurring of the subject's data 72. The function may be generated as a two-dimensional (2D) function for each voxel, or as a three-dimensional (3D) function for all voxels.

In graph 73 of FIG. 7, the amount of an acquired signal corresponding to the amount of acquired subject's data is a value of a location 731 on the x-axis. A location 732 on the y-axis represents a blur kernel value of a function corresponding to the location 731. The apparatus 50 applies the value of a location 732 to the subject's data 72 to remove a blur in the subject's data 72. The apparatus 50 uses a function to determine a blur kernel value to be applied for each voxel and applies the blur kernel value to deblurring. For example, the apparatus 50 may use the function to apply a blur kernel value, which is continuous for the amount of acquired subject's data, to the subject's data 72.

Figure 8:
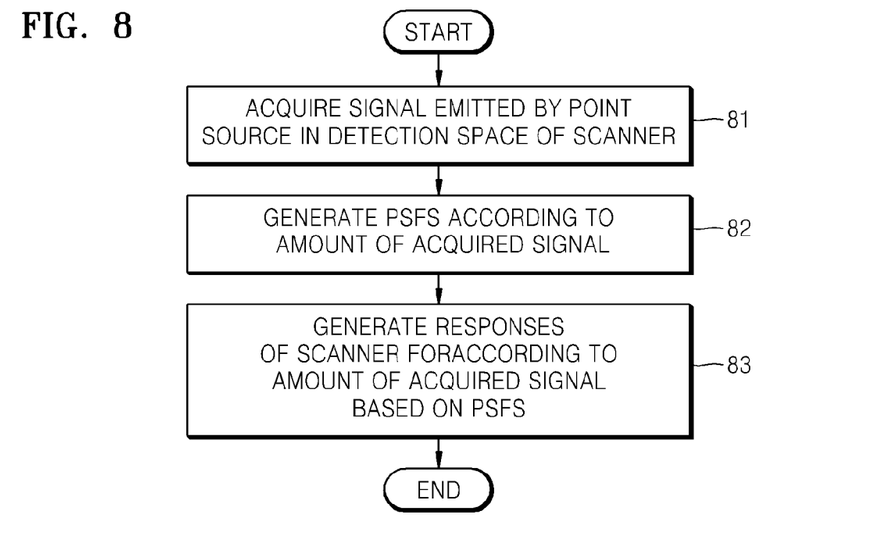
FIG. 8 is a flowchart of a method of generating a system response in the apparatus of FIG. 4 according to an illustrative example.

FIG. 8 is a flowchart of a method of generating a response in the apparatus 40 of FIG. 4. Referring to FIG. 8, the method of generating a system response includes operations performed by the apparatus 40 in a time series manner. Thus, although omitted herein, the descriptions with respect to the apparatus 40 apply to the descriptions of the method of generating a response with reference to FIG. 8.

Referring to FIGS. 4 and 8, the scanner 41 acquires a signal emitted by a point source in a detection space thereof (operation 81). The signal emitted by the point source may be acquired from all or some of the space in the scanner 41. When a signal is acquired from some of the space in the scanner 41, signals for the remaining space may be assumed based on the acquired signals. In this example, since the scanner 41 has a symmetrical cylindrical shape, a signal may be acquired from some of the space in the scanner 41 and may be assumed for the remaining space.

The PSF generator 42 creates a PSF for the amount of a signal acquired (operation 82). The PSF generator 42 generates a PSF which varies as the amount of a signal emitted by the point source and acquired from the scanner 41 increases.

The system response generator 43 generates a system response of the scanner 41 according to the amount of the acquired signal based on the PSF (operation 83).

Figure 9:
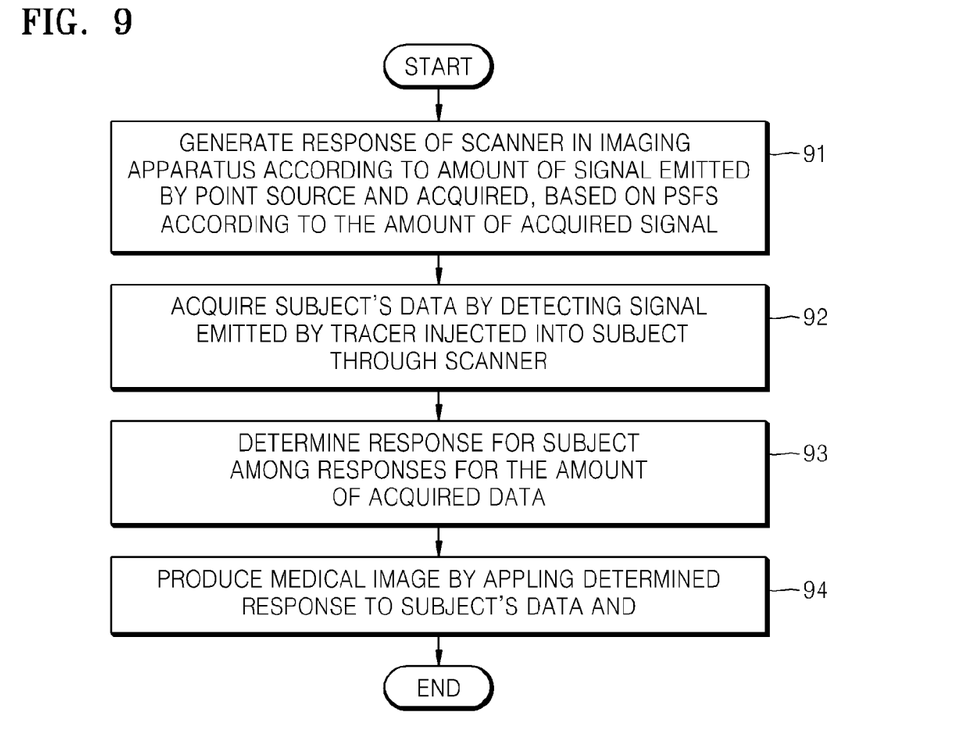
FIG. 9 is a flowchart of a method of generating a medical image in the apparatus of FIG. 5 according to an illustrative example.

FIG. 9 is a flowchart of a method of generating a medical image in the apparatus of FIG. 5. Referring to FIG. 9, the method of generating a medical image includes operations performed by the apparatus 50 in a time series manner. Thus, although omitted herein, the descriptions with respect to the apparatus 50 may apply to the descriptions of the method of generating a medical image with reference to FIG. 9.

Referring to FIGS. 5 and 9, the response generator 51 generates a response of a scanner corresponding to the amount of a signal acquired, based on a PSF created according to the amount of the acquired signal (operation 91). The response generator 51 may generate a response before imaging of a subject. The response generator 51 then outputs the response to the determination unit 53.

The data acquisition unit 52 receives a signal from the scanner which is emitted by a tracer injected into the subject and acquires a subject's data (operation 92). The data acquisition unit 52 then outputs the acquired subject's data to the determination unit 53.

The determination unit 53 determines a response for the subject among responses, according to the amount of acquired data (operation 93). For example, the determination unit 53 receives responses and the subject's data and determines a response to be applied to the subject's data.

The image reconstruction unit 54 applies the determined response to the subject's data to generate a medical image (operation 94). That is, the image reconstruction unit 54 applies the response inversely to the subject's data to produce a medical image.

The above examples and can be recorded in programs that can be executed on a computer and be implemented through general purpose digital computers which can run the programs using a computer-readable recording medium. Data structures described above can also be recorded on a medium in a variety of ways, with examples of the medium including recording media, such as magnetic storage media (e.g., ROM, RAM, USB, floppy disks, hard disks, etc.) and optical recording media (e.g., CD-ROMs, or DVDs).

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of generating a response from a scanner in an imaging apparatus, the method comprising:
    generating point spread functions (PSFs) according to an amount of a signal from a point source; and
    generating responses from the scanner according to the amount of the signal based on the PSFs.

2. The method of claim 1, wherein the generating of the PSFs comprises:
    presetting reference values according to the amount of the signal, and generating PSFs for the reference values until the amount of the signal reaches a reference value.

3. The method of claim 2, wherein the generating of the response comprises:
    producing matrices for the reference values by application of the PSFs.

4. The method of claim 3, further comprising:
    storing the matrices in a memory in the form of a look-up table.

5. The method of claim 1, wherein the generating of the response comprises:
    generating a function representing a degree of blur according to the amount of the signal, based on the PSFs.

6. A method of generating a medical image, the method comprising:
    generating responses from a scanner based on point spread functions (PSFs) created according to an amount of a signal emitted by a point source, wherein the responses correspond to the amount of the signal;
    detecting a signal emitted by a tracer introduced into a subject while in the scanner to acquire data of a subject;
    determining a response for the subject among the generated responses according to the amount of the data of the subject data; and
    producing a medical image by applying the determined response to the data of the subject.

7. The method of claim 6, wherein the generating of the responses comprises:
    presetting reference values according to the amount of the signal and generating the PSFs until the amount of the signal reaches a reference value.

8. The method of claim 7, wherein the generating of the responses includes generating matrices for the reference values by application of the PSFs.

9. The method of claim 8, wherein the determination of the response for the subject comprises determining a matrix for a reference value that is closest to the amount of the acquired data and determining a frame as a response, wherein the frame is generated at a location of a detection space corresponding to a voxel in the data of the subject, among frames in the determined matrix.

10. The method of claim 9, wherein the generating of the medical image further comprises: using the determined matrix to de-blur the data of the subject.

11. The method of claim 8, further comprising:
    storing the matrices in a memory in the form of a look-up table.

12. The method of claim 6, wherein the generating of the responses comprises generating functions, representing a degree of blur according to the amount of the acquired signal, based on the PSFs, and
    wherein in the generating of the response for the subject, the degree of blur according to the amount of the acquired data in the function is determined as the response for the subject.

13. An apparatus configured to generate a response in an imaging apparatus, the apparatus comprising:

a point spread function (PSF) generator configured to generate PSFs according to an amount of the signal from the point source; and a response generator configured to generate responses of the scanner according to the amount of the acquired signal based on the PSFs.

14. The apparatus of claim 13, wherein the PSF generator is configured to preset reference values according to the amount of the acquired signal and generates PSFs for each of the reference values when the amount of the acquired signal reaches the reference value, and wherein the response generator is configured to generate matrices for the reference values by using the PSFs.

15. The apparatus of claim 14, further comprising:
a memory configured to store the matrices in the form of a look-up table.

16. The apparatus of claim 13, wherein the response generator is configured to generate functions representing the degree of blur according to the amount of the acquired signal based on the PSFs.

17. The apparatus of claim 13, wherein the PSF generator generates PSFs for a voxel according to an increase in the amount of the acquired signal.

18. An apparatus configured to generate a medical image, the apparatus comprising:

a response generator configured to generate responses of a scanner in an imaging apparatus, according to the amount of a signal emitted by a point source and acquired from the scanner, based on point spread functions (PSFs) created according to the amount of the acquired signal;

a data acquisition unit configured to acquire data of the subject by receiving a signal emitted by a tracer introduced into a subject from the scanner;

a determination unit configured to determine a response for the subject among the generated responses, according to the amount of the subject's data acquired; and an image reconstruction unit configured to produce a medical image by applying the determined response to the data of the subject.

19. The apparatus of claim 18, wherein the response generator is configured to generate matrices for reference values by the PSFs and wherein the determination unit is configured to determine a matrix for a reference value that is closest to the amount of the acquired data and determines a frame as a response, which is generated at a location of a detection space corresponding to a voxel in the data of the subject, among frames in the determined matrix.

20. The apparatus of claim 19, wherein the image reconstruction unit is configured to use the determined matrix in deblurring of the data of the subject.

21. The apparatus of claim 18, wherein the determination unit is configured to generate functions, which represent the degree of blur according to the amount of the acquired signal, based on the PSFs, and determines the degree of blur for the amount of the acquired data in the function as the response for the subject.

* * * * *